(12) United States Patent
Kashiwagi et al.

(10) Patent No.: US 6,911,513 B2
(45) Date of Patent: Jun. 28, 2005

(54) FLUORINATED DIENE COMPOUND AND FLUOROPOLYMER, AND METHODS FOR THEIR PRODUCTION

(75) Inventors: Kimiaki Kashiwagi, Kanagawa (JP); Gen Ogawa, Kanagawa (JP); Takashi Okazoe, Kanagawa (JP); Kunio Watanabe, Kanagawa (JP); Eisuke Murotani, Kanagawa (JP); Kazuya Oharu, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/834,076

(22) Filed: Apr. 29, 2004

(65) Prior Publication Data

US 2004/0204615 A1 Oct. 14, 2004

Related U.S. Application Data

(63) Continuation of application No. PCT/JP02/11311, filed on Oct. 30, 2002.

(30) Foreign Application Priority Data

Oct. 31, 2001 (JP) .................................... 2001-334352

(51) Int. Cl.[7] ............................................. C08F 136/16
(52) U.S. Cl. ..................... 526/252; 526/72; 526/253; 526/247; 568/683
(58) Field of Search ..................... 526/252, 72, 253, 526/247; 568/683

(56) References Cited

U.S. PATENT DOCUMENTS

| 5,475,071 A | * | 12/1995 | Smart et al. ................ 526/252 |
| 5,589,557 A | * | 12/1996 | Navarrini et al. ........... 526/247 |
| 6,166,125 A | * | 12/2000 | Sugiyama et al. .......... 524/462 |
| 6,266,475 B1 | | 7/2001 | Suzuki et al. ................ 385/145 |
| 6,448,452 B2 | | 9/2002 | Kashiwagi et al. ......... 568/683 |
| 6,490,400 B2 | | 12/2002 | Suzuki et al. ................ 385/145 |
| 6,586,626 B2 | | 7/2003 | Okazoe et al. ............... 562/863 |
| 6,594,431 B2 | | 7/2003 | Suzuki et al. ................ 385/129 |
| 6,670,511 B2 | * | 12/2003 | Kashiwagi et al. .......... 568/683 |

FOREIGN PATENT DOCUMENTS

| EP | 303292 | * | 2/1989 |
| EP | 907088 | * | 4/1999 |
| EP | 1440961 A1 | * | 7/2004 |
| JP | 1-143843 | | 6/1989 |
| JP | 2000-81519 | * | 3/2000 |
| WO | WO 01/46093 | | 6/2001 |

OTHER PUBLICATIONS

PCT/JP2002/011311 search report.*
U.S. Appl. No. 10/307,392, filed Dec. 2, 2002, Kashiwagi et al.
U.S. Appl. No. 10/421,924, filed Apr. 24, 2003, Okazoe et al.

* cited by examiner

*Primary Examiner*—David W. Wu
*Assistant Examiner*—Henry S Hu
(74) *Attorney, Agent, or Firm*—Oblon Spivak McClelland Maier & Neustadt, P.C.

(57) ABSTRACT

A novel fluoropolymer which can be an optical resin material having a low refractive index and excellent heat resistance, and a novel fluorinated diene compound having two unsaturated bonds, capable of presenting such a fluoropolymer, are presented. Further, by virtue of the low refractive index and excellent heat resistance, the polymer presents a high performance optical transmitter and a plastic optical fiber.

A fluorinated diene compound represented by $CF_2=CFCF(OR^f)CF_2OCF=CF_2$ (wherein $R^f$ is a perfluoroalkyl group such as a trifluoromethyl group), and a fluoropolymer thereof. Further, an optical transmitter made by using such a fluoropolymer, and a plastic optical fiber having a core comprising such a fluoropolymer and a fluorinated low molecular weight compound contained therein as a refractive index-increasing agent.

10 Claims, No Drawings

FLUORINATED DIENE COMPOUND AND FLUOROPOLYMER, AND METHODS FOR THEIR PRODUCTION

This application is a continuation of International Application No. PCT/JP02/11311 filed Oct. 30, 2002.

TECHNICAL FIELD

The present invention relates to a fluorinated diene compound having two unsaturated bonds, and a method for its production, as well as a fluoropolymer, a fluoropolymer solution employing it, an optical transmitter and a plastic optical fiber.

BACKGROUND ART

As a fluorinated diene compound having two carbon—carbon unsaturated double bonds (hereinafter referred to as unsaturated bonds), $CF_2=CF(CF_2)_kOCF=CF_2$ (wherein k is an integer of from 1 to 3) is known (JP-A-1-143843). By cyclopolymerization of this compound, it is possible to obtain an amorphous polymer. Such a polymer has high elastic modulus, yield and breaking elongation and is tough and excellent also in impact resistance. Further, it has high transparency, and it is useful for an optical material for e.g. optical fibers and optical waveguides. However, the optical material employing this polymer has a low glass transition temperature ($T_g$) and thus has a drawback that the optical characteristics are likely to change when it is used at a high temperature for a long period of time. Accordingly, it is desired to develop a material having a higher $T_g$.

It is an object of the present invention to provide a novel polymer which not only maintains the mechanical properties which the above-mentioned amorphous polymer has, but also has a higher glass transition temperature, so that it can be an optical resin material having a low refractive index and being excellent in heat resistance, and a novel fluorinated diene compound having two unsaturated bonds, which presents such a polymer. Further, it is an object of the present invention to provide a high performance light transmitter and a plastic optical fiber, which have a low refractive index and excellent heat resistance.

DISCLOSURE OF THE INVENTION

As a result of an extensive study, the present inventors have produced a new specific fluorinated diene compound and further have found it possible to accomplish the above objects by polymerizing this fluorinated diene compound. That is, the present invention provides the following:

1. A fluorinated diene compound represented by the following formula (1):

$$CF_2=CFCF(OR^f)CF_2OCF=CF_2 \qquad (1)$$

wherein $R^f$ is a perfluoroalkyl group.

2. The fluorinated diene compound, wherein $R^f$ is a trifluoromethyl group.

3. A method for producing a fluorinated diene compound represented by the following formula (1), characterized in that a dehalogenation reaction is carried out at halogen atoms other than fluorine atoms in at least one compound selected from a compound represented by the following formula (2) and a compound represented by the following formula (3):

$$CF_2=CFCF(OR^f)CF_2OCF=CF_2 \qquad (1)$$

$$CF_2Z^1CFZ^2CF(OR^f)CF_2OCF=CF_2 \qquad (2)$$

$$CF_2Z^1CFZ^2CF(OR^f)CF_2OCFZ^3CF_2Z^4 \qquad (3)$$

wherein $R^f$ is a perfluoroalkyl group, and each of $Z^1$, $Z^2$, $Z^3$ and $Z^4$ which are independent of one another, is a halogen atom other than a fluorine atom.

4. A fluoropolymer comprising monomer units formed by cyclopolymerization of a fluorinated diene compound represented by the formula (1), or monomer units formed by cyclopolymerization of a fluorinated diene compound represented by the formula (1) and monomer units formed by polymerization of other monomer polymerizable with the fluorinated diene compound represented by the formula (1):

$$CF_2=CFCF(OR^f)CF_2OCF=CF_2 \qquad (1)$$

wherein $R^f$ is a perfluoroalkyl group.

5. The fluoropolymer, wherein $R^f$ is a trifluoromethyl group.

6. The fluoropolymer, wherein the monomer units formed by the cyclopolymerization of the fluorinated diene monomer represented by the formula (1), are monomer units represented by any one of the following formulae, wherein $R^f$ is as defined above:

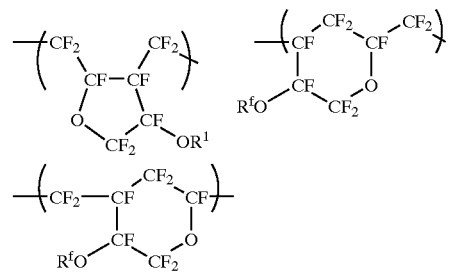

7. The fluoropolymer, wherein the monomer units of other polymerizable monomer are monomer units formed by polymerization of at least one member selected from a fluorinated diene which is cyclopolymerizable, other than the fluorinated diene compound represented by the formula (1), a monomer having a fluorinated aliphatic cyclic structure, a fluorinated non-cyclic vinyl ether monomer and a fluoroolefin.

8. The fluoropolymer, wherein the other monomer units are monomer units formed by polymerization of at least one member selected from tetrafluoroethylene, perfluoro (butenyl vinyl ether) and perfluoro(2,2-dimethyl-1,3-dioxole).

9. A fluoropolymer solution having the fluoropolymer dissolved in at least one fluorocarbon solvent selected from perfluoro(2-butyltetrahydrofuran), perfluorooctane, perfluorohexane, perfluoro(tributylamine), perfluoro(tripropylamine), perfluorobenzene and dichloropentafluoropropane.

10. An optical transmitter made by using the fluoropolymer.

11. A plastic optical fiber having a core formed of a mixture comprising the fluoropolymer and a fluorinated low molecular compound as a refractive index-increasing agent.

12. The plastic optical fiber, wherein the fluorinated low molecular compound is at least one compound selected from perfluoro(triphenyltriazine), perfluoro(1,3,5-triphenylbenzene) and a chlorotrifluoroethylene oligomer.

13. The plastic optical fiber, wherein the plastic optical fiber is a refractive index distribution optical fiber.

BEST MODE FOR CARRYING OUT THE INVENTION

The fluorinated diene compound of the present invention is a compound represented by the formula (1) (hereinafter, the compound represented by the formula (1) may be referred to also as the compound (1), and compounds represented by other formulae may likewise be referred to.). In the formulae, $R^f$ represents a perfluoroalkyl group.

The perfluoroalkyl group (hereinafter, the perfluoroalkyl group may be referred to as a $R^f$ group) is a group having all of hydrogen atoms of an alkyl group substituted by fluorine atoms. The structure of the $R^f$ group may, for example, be a linear structure, a branched structure, a cyclic structure or a structure having a partially cyclic structure.

As the $R^f$ group having a linear structure, a $R^f$ group having from 1 to 8 carbon atoms, is preferred, and it may, for example, be —$CF_3$, —$CF_2CF_3$, -n$C_3F_7$, -n$C_4F_9$, -n$C_5F_{11}$, -n$C_6F_{13}$, -n$C_7F_{15}$ or -n$C_8F_{17}$, and particularly preferred is —$CF_3$.

As the $R^f$ group having a branched structure, —$CF(CF_3)_2$, -iso$C_4F_9$, -sec$C_4F_9$ or -tert$C_4F_9$ may, for example, be mentioned.

As $R^f$ having a cyclic structure (i.e. a perfluorocycloalkyl group), a perfluorocyclopropyl group, a perfluorocyclobutyl group, a perfluorocyclopentyl group, a perfluorocyclohexyl group or a group having a perfluoroalkyl group having a linear structure or branched structure bonded to a carbon atom constituting the ring of such a group, may be mentioned.

As the $R^f$ group having a partially cyclic structure, a group having perfluorinated an alkyl group having a linear structure substituted by a cycloalkyl group, or a group having perfluorinated an alkyl group having a branched structure substituted by a cycloalkyl group may be mentioned, and, for example, a perfluoro(cyclohexylmethyl) group or a perfluoro(cyclohexylethyl) group is preferred.

$R^f$ in the compound (1) of the present invention is particularly preferably a trifluoromethyl group.

The following compounds may be mentioned as specific examples of the compound (1) of the present invention.

$CF_2=CFCF(OCF_3)CF_2OCF=CF_2$

$CF_2=CFCF(OCF_2CF_3)CF_2OCF=CF_2$

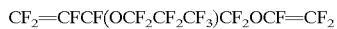

$CF_2=CFCF(OCF_2CF_2CF_3)CF_2OCF=CF_2$

$CF_2=CFCF(OCF_2CF_2CF_2CF_3)CF_2OCF=CF_2$

$CF_2=CFCF(OCF(CF_3)_2)CF_2OCF=CF_2$

$CF_2=CFCF(OCF_2CF(CF_3)_2)CF_2OCF=CF_2$

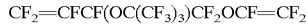

$CF_2=CFCF(OC(CF_3)_3)CF_2OCF=CF_2$

The fluorinated diene compound of the present invention is preferably produced by a method wherein a dehalogenation reaction is carried out at halogen atoms other than fluorine atoms in at least one compound selected from a compound represented by the following formula (2) and a compound represented by the following formula (3):

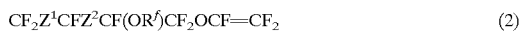

$CF_2Z^1CFZ^2CF(OR^f)CF_2OCF=CF_2$ (2)

$CF_2Z^1CFZ^2CF(OR^f)CF_2OCFZ^3CF_2Z^4$ (3)

In the above formulae, $R^f$ is a perfluoroalkyl group corresponding to $R^f$ in the formula (1).

Further, each of $Z^1$, $Z^2$, $Z^3$ and $Z^4$ which are independent of one another, is a halogen atom other than a fluorine atom, and may, for example, be a chlorine atom, a bromine atom or an iodine atom, preferably a chlorine atom or a bromine atom, particularly preferably each being a chlorine atom. By the dehalogenation of such halogen atoms, a double bond will be formed, whereby a fluorinated diene compound represented by the formula (1) will be formed.

The dehalogenation in the method for producing a fluorinated diene compound of the present invention, is preferably carried out by having a dehalogenating agent reacted in a polar solvent. The dehalogenating agent is a reactive agent which reacts with halogen atoms in a substrate to withdraw the halogen atoms. Such a dehalogenating agent may, for example, be zinc, sodium, magnesium, tin, copper, iron or other metals. Zinc is particularly preferred from the viewpoint of such a reaction condition that a relatively low reaction temperature can be thereby employed.

As the polar solvent, an organic polar solvent such as dimethylformamide, 1,4-dioxane, diglime or methanol, or water, is preferred.

The amount of the dehalogenating agent is preferably from 1 to 20 times by mol, particularly preferably from 1 to 10 times by mol, especially preferably from 2 to 10 times by mol, based on the total amount of the compound (2) and/or the compound (3) to be used for the reaction. The reaction temperature is usually from 40 to 100° C., preferably from 50 to 80° C. The dehalogenation reaction is usually carried out by dropwise adding the compound (2) in the presence of the dehalogenating agent and the solvent. Isolation of the reaction product is preferably carried out by withdrawing the reaction product from the reaction system quickly after the reaction, by reactive distillation.

As a preferred embodiment of the compound (2) wherein $R^f$ is a trifluoromethyl group and each of $Z^1$ and $Z^2$ is a chlorine atom, the following compound (2-1) can be obtained by pyrolyzing the compound (2-2). This compound (2-2) can be synthesized by adding hexafluoropropylene oxide to the compound (2-3):

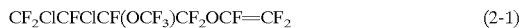

$CF_2ClCFClCF(OCF_3)CF_2OCF=CF_2$ (2-1)

$CF_2ClCFClCF(OCF_3)CF_2OCF(CF_3)COF$ (2-2)

$CF_2ClCFClCF(OCF_3)COF$ (2-3)

The compound (2-3) is preferably produced by the following method 1 or 2.

Method 1:

A method wherein the following compound (A) and the following compound (B) are subjected to an esterification reaction to form the following compound (C), the compound (C) is fluorinated to form the following compound (D), and the compound (D) is subjected to decomposition of the ester bond.

$CH_2ClCHClCH(OCH_3)CH_2OH$ (A)

$R^{f2}COX$ (B)

$CH_2ClCHClCH(OCH_3)CH_2OCOR^{f2}$ (C)

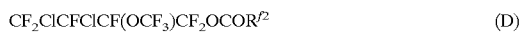

$CF_2ClCFClCF(OCF_3)CF_2OCOR^{f2}$ (D)

In the above formulae, $R^{f2}$ is a perfluoro monovalent saturated organic group, and X is a halogen atom.

Method 2:

A method wherein the following compound ($A^1$) is reacted with the following compound (B) for esterification to form the following compound ($C^1$), the compound ($C^1$) is chlorinated to form the following compound (C), the compound (C) is fluorinated to form the following compound (D), and the compound (D) is subjected to decomposition of the ester bond.

$CH_2=CHCH(OCH_3)CH_2OH$ (A¹)

$R^{f2}COX$ (B)

$CH_2=CHCH(OCH_3)CH_2OCOR^{f2}$ (C¹)

$CH_2ClCHClCH(OCH_3)CH_2OCOR^{f2}$ (C)

$CF_2ClCFClCF(OCF_3)CF_2OCOR^{f2}$ (D)

In the above formulae, X is a halogen atom, and $R^{f2}$ is a perfluoro monovalent saturated organic group.

$R^{f2}$ is preferably a perfluoroalkyl group, a perfluoro(etheric oxygen atom-containing alkyl) group, a perfluoro(partially chloroalkyl) group, or a perfluoro(partially chloro(etheric oxygen atom-containing alkyl)) group, particularly preferably a perfluoro(partially chloro(etheric oxygen atom-containing alkyl)) group, especially preferably $CF_2ClCFClCF(OCF_3)CF_2-$.

As specific examples of $R^{f2}$, the following groups may be mentioned, wherein n is an integer of from 1 to 9, r is an integer of from 0 to 10, each of m and p is an integer of at least 0, preferably an integer of from 0 to 10, and k is an integer of at least 1, preferably an integer of from 1 to 10.

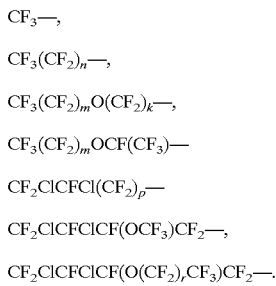

$CF_3-$, $CF_3(CF_2)_n-$, $CF_3(CF_2)_mO(CF_2)_k-$, $CF_3(CF_2)_mOCF(CF_3)-$ $CF_2ClCFCl(CF_2)_p-$ $CF_2ClCFClCF(OCF_3)CF_2-$, $CF_2ClCFClCF(O(CF_2)_rCF_3)CF_2-$.

Further, as $R^{f2}$, $CF_2ClCFClCF(OCF_3)-$ is preferred.

X is a fluorine atom, a chlorine atom, a bromine atom or an iodine atom, preferably a fluorine atom, a chlorine atom or a bromine atom, particularly preferably a fluorine atom.

In the above methods 1 and 2, the esterification reaction can be carried out under conditions for a usual esterification reaction. Such a reaction may be carried out by using a solvent (hereinafter referred to as an esterification solvent), but it is preferred not to use an esterification solvent, from the viewpoint of the volume efficiency.

In the esterification reaction, HX will be formed as a by-product. When X is a fluorine atom, HF will be formed as a by-product, and as a HF scavenger, an alkali metal fluoride (such as NaF, KF or the like) or a base such as a trialkylamine or pyridine, may be present in the reaction system. In a case where such a HF scavenger is employed, its amount is preferably from 1 to 10 times by mol, to the compound (B) or the compound (B¹). In a case where no such a HF scavenger is used, the reaction may be carried out at a reaction temperature where HF can be vaporized, and HF is discharged out of the system as carried by a nitrogen stream.

The lower limit temperature for the esterification reaction is, in a usual case, preferably at least −50° C., and the upper limit is preferably whichever is lower +100° C. or the boiling point of the esterification solvent. Further, the reaction time may optionally be changed depending upon the supply rate of the raw material and the amount of the compound to be used for the reaction. The reaction pressure (the gauge pressure, the same applies hereinafter) is preferably from 0 to 2 MPa.

In the method 2, the compound (C¹) formed by the esterification reaction, is chlorinated to form the compound (C). The chlorination reaction can be carried out under the operational and reaction conditions for a usual chlorination reaction by means of a chlorinating agent. The chlorinating agent is preferably chlorine ($Cl_2$). In a case where chlorine is used, the amount is preferably from 1 to 10 times by mol, particularly preferably from 1 to 5 times by mol, to the compound (C¹). The reaction of the compound (C¹) with the chlorinating agent may be carried out by using a solvent (hereinafter referred to as a chlorination solvent), but it is preferred not to use a chlorination solvent from the viewpoint of the volume efficiency. In a case where a chlorination solvent is employed, it is preferred to employ a halogenated hydrocarbon solvent. The halogenated hydrocarbon solvent may, for example, be dichloromethane or chloroform. The amount of the chlorination solvent is preferably from 0.5 to 5 times the mass of the compound (C¹). Further, the temperature for the chlorination reaction is preferably from −78° C. to +200° C.

With respect to the compound (C) in the methods 1 and 2, a fluorination reaction is then carried out. The fluorination reaction may be carried out by an electrochemical fluorination method (ECF method), a method for fluorination by means of cobalt fluoride, or a method for a reaction with fluorine gas in a gas phase, but such methods have various problems such that the yield of the fluorinated reaction product is very small, a special apparatus is required, the operation is difficult, etc. Accordingly, in the present invention, it is preferred to employ a liquid phase fluorination method wherein a reaction with fluorine is carried out in a liquid phase, from the viewpoint of a high yield, simplicity of the operation, etc. Now, the liquid phase fluorination method will be described.

The fluorine content in the compound (C) is preferably appropriately changed depending upon the type of the liquid phase to be used for the fluorination reaction. The lower limit of the fluorine content (the proportion of the total amount of fluorine atoms to the molecular weight of the substrate to be fluorinated) is usually preferably 10 mass %, particularly preferably 30 mass %. Further, the upper limit is preferably 86 mass %, particularly preferably 80 mass %.

Further, it is preferred to adjust the structure of $R^{f2}$ so that the molecular weight of the compound (C) will be from 300 to 1000. It is preferred that the molecular weight is within the above range, since the fluorination reaction in the liquid phase can be carried out smoothly. If the molecular weight is too small, the substrate to be fluorinated, tends to be easily vaporized, whereby a decomposition reaction in a gas phase is likely to take place during the fluorination reaction in the liquid phase. On the other hand, if the molecular weight is too large, purification of the substrate to be fluorinated tends to be difficult.

The following compounds may be mentioned as examples of the compound (C) and the compound (C¹) as substrates to be fluorinated. Here, m in the following formulae is as defined above.

$CH_2ClCHClCH(OCH_3)CH_2OCOCF(CF_3)O(CF_2)_mCF_3$, $CH_2ClCHClCH(OCH_3)CH_2OCOCF_2CF(OCF_3)CFClCF_2Cl$, $CH_2=CHCH(OCH_3)CH_2OCOCF(CF_3)O(CF_2)_mCF_3$, $CH_2=CHCH(OCH_3)CH_2OCOCF_2CF(OCF_3)CFClCF_2Cl$.

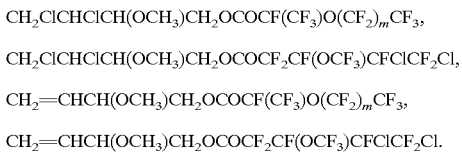

The liquid phase fluorination is preferably carried out by introducing fluorine in the solvent constituting the liquid phase and reacting it with the compound. As the fluorine, 100% fluorine gas may be employed, or fluorine gas diluted with an inert gas may be employed. As such an inert gas, nitrogen gas or helium gas is preferred, and nitrogen gas is particularly preferred. The fluorine gas content in the gas mixture of the inert gas and the fluorine gas, is preferably at least 5 vol % from the viewpoint of the efficiency, particularly preferably from 5 to 30 vol % from the viewpoint of withdrawing chlorine or preventing migration of chlorine.

As the solvent (hereinafter referred to as a fluorination solvent), a solvent which essentially contains a C—F bond without containing a C—H bond, is preferred. Further, a perfluoroalkane or an organic solvent obtained by perfluorinating a known organic solvent having in its structure at least one atom selected from a chlorine atom, a nitrogen atom and an oxygen atom, is preferred. Further, as the fluorination solvent, it is preferred to employ a solvent having a high solubility of the compound (C), and it is particularly preferred to employ a solvent capable of dissolving at least 1 mass %, particularly preferably at least 5 mass %, of the compound (C), based on the total amount of the solvent and the compound (C).

Examples of such a fluorination solvent include the compound (D) as a product of a fluorination reaction, the compound (B), perfluoroalkanes (trade name: FC-72, etc.), perfluoroethers (trade name: FC-75, FC-77, etc.), perfluoropolyethers (trade name: KRYTOX, FOMBLIN, GALDEN, DEMNUM, etc.), chlorofluorocarbons (trade name: FLON LUBE), chlorofluoropolyethers, perfluoroalkylamines (such as perfluorotrialkylamine, etc.), and inert fluids (trade name: FLUORINERT). Among them, the compound (D) is preferred as the fluorination solvent. When the compound (D) is used, there will be an advantage that post treatment after the reaction may be easy. The amount of the fluorination solvent is preferably at least 5 times by mass, particularly preferably from 10 to 100 times by mass, relative to the compound (C).

The reaction system for the liquid phase fluorination reaction is preferably a batch system or a continuous system. From the viewpoint of the yield and selectivity of the reaction, the reaction system is preferably the following system 2. Further, as the fluorine gas, one diluted with an inert gas such as nitrogen gas may be employed either in a case where the reaction is carried out by a batch system or a case where the reaction is carried out by a continuous system. The following systems may be mentioned as methods for the fluorination reaction by a continuous system.

System 1

A method wherein into a reactor, the compound (C) and the fluorination solvent are charged, and stirring is initiated. Then, the reaction is carried out while continuously supplying fluorine gas into the fluorination solvent at the prescribed reaction temperature and reaction pressure.

System 2

A method wherein into a reactor, the fluorination solvent is charged and stirred, and then the compound (C) and fluorine gas are continuously and simultaneously supplied into the fluorination solvent in a prescribed molar ratio at a predetermined reaction temperature and reaction pressure.

When supplying the compound (C), it may or may not be diluted with the fluorination solvent. In a case where it is diluted, the amount of the fluorination solvent to the mass of the compound (C) is preferably adjusted to be at least 5 times, particularly preferably at least 10 times.

In the liquid phase fluorination reaction, in order to let the fluorination reaction proceed efficiently, it is preferred to charge fluorine gas so that at a later stage of the reaction, the amount of fluorine will be always excess in equivalent to hydrogen atoms present in the compound (C) and it is particularly preferred to charge fluorine gas so that it will be at least 1.5 times by equivalent (i.e. at least 1.5 times by mol), from the viewpoint of the selectivity. The amount of fluorine is preferably maintained to be always in excess from the initiation to the end of the reaction.

The reaction temperature for the liquid phase fluorination reaction is preferably at least −60° C. and at most the boiling point of the compound (C). It is particularly preferably from −50° C. to +100° C. from the viewpoint of the yield by the reaction, the selectivity and the industrial operation efficiency, and it is especially preferably from −20° C. to +50° C. from the viewpoint of withdrawing chlorine or preventing migration of chlorine. The reaction pressure for the fluorination reaction is not particularly limited, and it is particularly preferably from atmospheric pressure to 2 MPa (gauge pressure, and the pressure will hereinafter be represented by a gauge pressure unless otherwise specified) from the viewpoint of the yield by the reaction, the selectivity and the industrial operation efficiency.

Further, in the liquid phase fluorination, it is preferred to let a C—H bond-containing compound be present in the reaction system, or to carry out irradiation with ultraviolet rays. For example, it is preferred to add the C—H bond-containing compound to the reaction system or to carry out irradiation with ultraviolet rays at a later stage of the fluorination reaction, whereby hydrogen atoms present in the compound (C), which are hardly fluorinated, can efficiently be fluorinated, and the conversion can remarkably be improved. The time for irradiation with ultraviolet rays is preferably from 0.1 to 3 hours.

The C—H bond-containing compound is preferably an organic compound other than the compound (C), particularly preferably an aromatic hydrocarbon, especially preferably benzene, toluene or the like. The amount of the C—H bond-containing compound is preferably from 0.1 to 10 mol %, particularly preferably from 0.1 to 5 mol %, based on the hydrogen atoms in the compound (C).

The C—H bond-containing compound is preferably added in a state where fluorine is present in the reaction system. Further, in a case where the C—H bond-containing compound is added, the reaction system is preferably pressurized. The pressurizing pressure is preferably from 0.01 to 5 MPa.

The liquid phase fluorination reaction is carried out until hydrogen atoms in the compound (C) are perfluorinated. In the liquid phase fluorination reaction, hydrogen atoms are replaced by fluorine atoms, and in a case where an unsaturated bond is present, fluorine atoms will be added to the unsaturated bond portion.

In the liquid phase fluorination reaction, HF will be formed as a by-product. In order to remove HF formed as a by-product, it is preferred to let a HF scavenger be coexistent in the reaction system or to contact a HF scavenger and the discharge gas at the gas outlet of the reactor. As such a HF scavenger, a base such as an alkali metal fluoride (such as NaF, KF or the like) is preferred, and such a base may be present in the reaction system. As the HF scavenger, NaF is particularly preferred.

In a case where the HF scavenger is incorporated in the reaction system, its amount is preferably from 1 to 20 times by mol, more preferably from 1 to 5 times by mol, to the total amount of hydrogen atoms present in the compound (C). In a case where the HF scavenger is disposed at the gas outlet of the reactor, it is preferred to install (a) a cooler (maintained to be preferably from 10° C. to room temperature, particularly preferably at about 20° C.), (b) a packed layer of the HF scavenger such as NaF pellets, and (c) a cooler (maintained to be preferably from −78° C. to +10° C., more preferably from −30° C. to 0° C.) in series in the order of (a)–(b)–(c). Further, a liquid-returning line may be installed to return a condensed liquid from the cooler (c) to the reactor.

Then, the compound (D) is subjected to a decomposition reaction of the ester bond to obtain the desired compound (2-3).

The decomposition reaction is a reaction to break —CF₂OCO— to form two —COF groups. Such a reaction is preferably carried out by a pyrolysis reaction or by a decomposition reaction carried out in the presence of a nucleophilic agent or an electrophilic agent.

The pyrolysis reaction can be carried out by heating the compound (D). The reaction system for the pyrolysis reaction is preferably selected depending upon the boiling point and stability of the compound (D).

For example, for a pyrolysis reaction in a case where the compound (D) is a compound which is easily vaporized, it is possible to employ a vapor phase pyrolysis method wherein decomposition is carried out in a vapor phase continuously, and the outlet gas containing the obtained compound (2-3) is condensed and recovered. The reaction temperature for the vapor phase pyrolysis method is preferably from 50 to 350° C., particularly preferably from 50 to 300° C., especially preferably from 150 to 250° C. Further, in the reaction system, an inert gas which is not directly involved in the reaction, may be present. As such an inert gas, nitrogen gas or carbon dioxide gas may, for example, be mentioned. The inert gas is preferably incorporated in an amount of from about 0.01 to 50 vol %, based on the compound (D). If the amount of the inert gas to be incorporated, is large, the recovery of the product may sometimes decrease.

On the other hand, for a pyrolysis reaction in a case where the compound (D) is a hardly vaporizable compound, it is preferred to employ a liquid phase pyrolysis method wherein the liquid is heated in the state of liquid in the reactor. The reaction pressure in such a case is not limited. In a usual case, products formed by decomposition of the ester bond have lower boiling points. Accordingly, it is preferred to carry out the reaction while continuously withdrawing the low boiling point products by means of a reactor equipped with a distillation column. Otherwise, a method may be employed wherein the products are withdrawn from the reactor all at once after completion of the heating. The reaction temperature for such a liquid phase pyrolysis method is preferably from 50 to 300° C., particularly preferably from 80 to 250° C.

In a case where pyrolysis is carried out by a liquid phase pyrolysis method, it may be carried out in the absence of a solvent or in the presence of a solvent (hereinafter referred to as a decomposition reaction solvent). However, it is preferred to carry out the reaction in the absence of any solvent. In a case where the decomposition reaction solvent is employed, the solvent is not particularly limited so long as it is a solvent which does not react with the compound (D) and is compatible with the compound (D) and which does not react with the compound (2-3). Further, as the decomposition reaction solvent, it is preferred to select one which can easily be separated at the time of purification of the product.

As a specific example of the decomposition reaction solvent, an inert solvent such as a perfluorotrialkylamine or perfluoronaphthalene, or a chlorotrifluoroethylene oligomer (such as FLON LUBE, trade name, manufactured by Asahi Glass Company, Limited) having a high boiling point among chlorofluorocarbons, is preferred. Further, the decomposition reaction solvent is preferably used in an amount of from 10 to 1000 mass %, based on the compound (D).

Further, the compound (D) may be subjected to decomposition of the ester bond by reacting it with a nucleophilic agent or an electrophilic agent in a liquid phase. In such a case, the reaction may be carried out in the absence of any solvent or in the presence of a decomposition reaction solvent. The nucleophilic agent is preferably a fluorine ion (F⁻), particularly preferably a fluorine ion derived from an alkali metal fluoride. As such an alkali metal fluoride, NaF, NaHF₂, KF or CsF is preferred, and particularly preferred is NaF. By carrying out the pyrolysis reaction in the presence of NaF, it is possible to carry out the pyrolysis reaction at a low temperature, whereby it is possible to prevent a decomposition reaction of the compound.

The nucleophilic agent to be used at the initial stage of the reaction, is preferably in a catalytic amount, but may be used in excess. The amount of the nucleophilic agent is preferably from 1 to 500 mol %, particularly preferably from 10 to 100 mol %, especially preferably from 5 to 50 mol %, based on the compound (D). The lower limit of the reaction temperature is preferably at least −30° C., and the upper limit is whichever is lower the boiling point of the solvent or the boiling point of the compound (D), and usually, it is particularly preferably from −20° C. to +250° C. The decomposition reaction is preferably carried out by means of a reactor equipped with a distillation column.

In the decomposition reaction of the ester bond, together with the compound (2-3), the compound (B) represented by the formula $R^{f2}COX$, will be formed.

The compound (B) wherein $R^{f2}$ is $CF_2ClCFClCF(OCF_3)CF_2$—, is the same as the compound of the formula (2-3), whereby no separation operation of the formed product is required. However, in a case where $R^{f2}$ is a group other than $CF_2ClCFClCF(OCF_3)CF_2$—, it is preferred to separate the compound (B) in the product. And, such a compound (B) is preferably reused as a compound (B) to be reacted with the compound (A) or the compound (A¹).

The reaction for adding hexafluoropropylene oxide to the compound (2-3) to obtain the compound (2-2), is preferably carried out by reacting a metal fluoride to the compound (2-3) in a solvent and reacting it with hexafluoropropylene oxide. The reaction temperature for the reaction is preferably at most 50° C., particularly preferably from 5 to 25° C. The metal fluoride may, for example, be potassium fluoride, cesium fluoride, sodium fluoride or silver fluoride. The solvent for the reaction is preferably an ether solvent or an aprotic polar solvent. The reaction pressure of hexafluoropropylene oxide is preferably from 0 to 1 MPa, particularly preferably from 0.1 to 0.5 MPa.

Further, the compound (2-2) can be synthesized from the compound (2-4) by the method disclosed in WO01/46093. Namely, the compound (2-4) is reacted with the compound (2-5) to obtain a compound (2-6). Further, the compound (2-6) is contacted with chlorine gas to obtain a compound (2-7). The compound (2-7) is subjected to liquid phase fluorination to obtain the compound (2-2).

  (2-2)

  (2-4)

  (2-5)

  (2-6)

  (2-7)

In the above formulae, $R^{f3}$ is preferably a fluoroalkyl group, a fluoro(partially chloroalkyl) group, a fluoro(hetero atom-containing alkyl) group or a fluoro(partially chloro (hetero atom-containing alkyl)) group, particularly preferably such a group which is perfluorinated.

The compound (2-2) will then be pyrolyzed to obtain the compound (2-1). The pyrolysis can be carried out by a method of directly pyrolyzing the compound (2-2), or a method of converting the compound (2-2) to an alkali salt of the corresponding carboxylic acid, followed by pyrolysis. Further, it is also possible to employ a method wherein the active group (—COF) in the compound (2-2) is converted to a practically stable group, which is then converted to an alkali salt of the carboxylic acid, followed by pyrolysis. As such a method, a method may, for example, be mentioned wherein the compound (2-2) is reacted with an alkanol to convert it to an alkyl ester of the corresponding carboxylic acid, which is then converted to an alkali salt, followed by pyrolysis.

In a case where the compound (2-2) is directly pyrolyzed, it is preferred that the compound (2-2) is vaporized, then if necessary, diluted with an inert gas such as nitrogen gas, and contacted with a solid basic salt or glass beads at a high temperature. The reaction temperature is usually from 200 to 500° C., particularly preferably from 250 to 350° C. As the solid basic salt, sodium carbonate, potassium carbonate or sodium phosphate may, for example, be used, and sodium carbonate is particularly preferred.

Whereas, in a case where the compound (2-2) is converted to an alkali metal salt of the corresponding carboxylic acid and then pyrolyzed, it is preferred firstly to react the compound (2-2) with an alkali metal hydroxide to form an alkali metal salt of the carboxylic acid. The pyrolysis reaction of this alkali metal salt is preferably carried out from 100 to 300° C., particularly preferably from 150 to 250° C. By the pyrolysis reaction, the compound (2-1) will be obtained. The pyrolysis reaction of an alkali metal salt of the carboxylic acid is preferred, since it can be carried out at a low temperature as compared with the method of carrying out the pyrolysis directly, and the yield is also high. The production of the alkali metal salt of the carboxylic acid is preferably carried out by using water or an alcohol as a solvent, and it is preferred that the obtained alkali metal salt is sufficiently dried and then pyrolyzed. Further, as the alkali metal salt, a sodium salt or a potassium salt may be mentioned, and a potassium salt is preferred, since it can be pyrolyzed at a lower temperature.

Further, the fluorinated diene compound (1) of the present invention can be obtained also by carrying out dehalogenation at halogen atoms other than fluorine atoms of the compound (3). A compound (3-1) as a preferred embodiment of the compound (3) wherein $R^f$ is a trifluoromethyl group, and $Z^1$, $Z^2$, $Z^3$ and Z are chlorine atoms, can be produced as follows. Namely, a compound (2-3) is esterified to produce a compound (3-2) (wherein R is an alkyl group). Otherwise, the compound (3-2) may also be obtained by ester exchange of the above-mentioned compound (D) and an alkanol represented by the formula ROH (wherein R is as defined above). Further, the compound (3-2) is reduced to obtain a compound (3-3). Then, this compound is reacted with an alkali metal hydride or an alkali metal to form a metal alkoxide (3-3a) (wherein M is an alkali metal atom), which is then reacted with tetrafluoroethylene to obtain a compound (3-4). This compound (3-4) is further contacted with chlorine gas to add chlorine atoms to the unsaturated bond thereby to produce a compound (3-5). Finally, hydrogen atoms in this compound (3-5) are all replaced by fluorine atoms by liquid phase fluorination to obtain the compound (3-1).

| | |
|---|---|
| $CF_2ClCFClCF(OCF_3)CF_2OCFClCF_2Cl$ | (3-1) |
| $CF_2ClCFClCF(OCF_3)COF$ | (2-3) |
| $CF_2ClCFClCF(OCF_3)CO_2R$ | (3-2) |
| $CF_2ClCFClCF(OCF_3)CH_2OH$ | (3-3) |
| $CF_2ClCFClCF(OCF_3)CH_2OM$ | (3-3a) |
| $CF_2ClCFClCF(OCF_3)CH_2OCF=CF_2$ | (3-4) |
| $CF_2ClCFClCF(OCF_3)CH_2OCFClCF_2Cl$ | (3-5) |

The esterification of the compound (2-3) can be carried out by dropwise adding the acid fluoride represented by the formula (2-3) into an alkanol represented by the formula ROH. The temperature for the reaction is preferably from 0° C. to 20° C. R is preferably a $C_{1-4}$ alkyl group. On the other hand, in a case where the compound (3-2) is produced by the ester exchange, usual ester exchange reaction conditions can be applied.

Then, the compound (3-2) is reduced to produce the compound (3-3). The reduction reaction is preferably carried out, for example, by sodium boron hydride or lithium aluminum hydride. The reaction temperature is preferably from 0° C. to 20° C. The reduction reaction is preferably carried out in the presence of a reaction solvent, and as the reaction solvent, an alcohol or a non-cyclic or cyclic ether solvent may be mentioned. Specifically, methanol, ethanol, isopropanol, n-butanol, t-butanol, diethyl ether, methyl t-butyl ether, tetrahydrofuran, dioxane, monoglime, diglime, triglime or tetraglime may, for example, be used. These solvents may be used alone or in combination as a mixture of an optional ratio. By mixing the solvent, it is possible to control the reaction. In the case of a mixture, it is preferred to employ an ether solvent in an amount of from 1 to 10 times by volume to an alcohol. To control a side reaction, it is particularly preferred to use diethyl ether or tetrahydrofuran as mixed in an amount of from 1 to 2 times by volume to ethanol.

Then, the compound (3-3) is reacted with an alkali metal hydride or an alkali metal (such as sodium) to obtain the compound (3-3a). The temperature for such a reaction is preferably from 0° C. to 20° C. The alkali metal atom in the alkali metal hydride may, for example, be sodium, lithium, potassium or cesium. Such a reaction may be carried out in the presence of a reaction solvent, and as such a reaction solvent, a non-cyclic or cyclic ether solvent or an aprotic polar solvent may be employed. Specifically, diethyl ether, methyl t-butyl ether, tetrahydrofuran, dioxane, monoglime, diglime, triglime, tetraglime, acetonitrile, benzonitrile, sulfolane, dimethylacetamide or dimethylsulfoxide may, for example, be used. The formed compound (3-3a) is preferably used for the next reaction together with the reaction solvent, without isolating it.

Then, tetrafluoroethylene is added to the compound (3-3a) to obtain the compound (3-4). This reaction is preferably carried out by transferring the reaction product containing the compound (3-3a) as it contains the reaction solvent, to an autoclave and introducing tetrafluoroethylene. The reaction temperature for the reaction is preferably from −10 to +50° C., particularly preferably from 0 to +30° C. The reaction pressure is preferably from 0.5 to 3.5 MPa, particularly preferably from 1.0 to 2.2 MPa. Further, it is preferred to raise the reaction temperature after completion of the introduction of tetrafluoroethylene, and the temperature raised is preferably from 30 to 100° C., particularly preferably from 50 to 70° C. The reaction time is preferably from 30 minutes to 120 hours, particularly preferably from 5 hours to 10 hours.

Then, the compound (3-4) is chlorinated to obtain the compound (3-5) having chlorine atoms introduced to the unsaturated double bond of the vinyl ether. This reaction involves heat generation, and it is accordingly preferred to carry out the reaction while cooling the system. The reaction temperature for this reaction is preferably adjusted from −50 to 100° C., particularly preferably from −20 to 10° C.

Then, the compound (3-5) is reacted with fluorine in a liquid phase to obtain the compound (3-1). This can be carried out in the same manner as the above-mentioned fluorination. And, the compound (3-1) is subjected to the above-mentioned dehalogenation reaction, whereby the compound (1) of the present invention can be produced.

The fluorinated diene compound (1) of the present invention is polymerizable, and is useful as a monomer for the production of a fluoropolymer. This fluorinated diene compound (1) undergoes cyclic polymerization alone by an action of a radical polymerization initiator to form a polymer having monomer units having fluorinated aliphatic cyclic structures in its main chain. Further, the fluorinated diene compound (1) may be copolymerized with another monomer.

Namely, the present invention presents a fluoropolymer comprising monomer units formed by cyclopolymerization of the fluorinated diene compound (1), or a fluoropolymer comprising monomer units formed by cyclopolymerization of the fluorinated diene compound (1) and monomer units formed by polymerization of another monomer polymerizable with the fluorinated diene compound (1). The proportion of the monomer units of the fluorinated diene compound (1) contained in the fluoropolymer is preferably from 30 to 100 mol %, particularly preferably from 50 to 100 mol %, based on the total monomer units. Further, the molecular weight of the fluoropolymer is preferably from 500 to $1 \times 10^6$, particularly preferably from 500 to $5 \times 10^5$.

The monomer units formed by cyclopolymerization of the fluorinated diene compound (1) are preferably either one of monomer units represented by the following formulae. The monomer units present in the fluoropolymer may be of one type, or of two or more types.

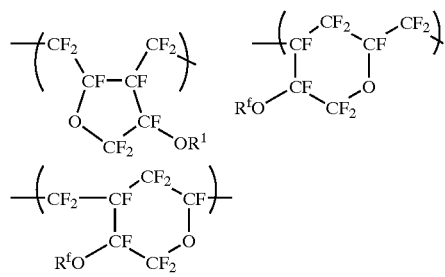

Another polymerizable monomer is not particularly limited so long as it is a radically polymerizable monomer, and it may, for example, be a fluorinated monomer other than the compound (1), a hydrocarbon monomer or other monomer. For example, it may be an olefin such as ethylene, a fluoroolefin such as tetrafluoroethylene, a fluorinated vinyl ether monomer such as a perfluoro(alkyl vinyl ether), a cyclopolymerizable fluorinated diene (other than the fluorinated diene compound (1)) such as a perfluoro(allyl vinyl ether) or a monomer having a fluorinated aliphatic ring structure, such as perfluoro(2,2-dimethyl-1,3-dioxole). As another polymerizable monomer, at least one member selected from tetrafluoroethylene, perfluoro(butenyl vinyl ether) and perfluoro(2,2-dimethyl-1,3-dioxole) is particularly preferred. The proportion of monomer units of another polymerizable monomer is preferably from 0 to 70 mol %, particularly preferably from 0 to 50%, based on the total monomer units in the fluoropolymer. Such another monomer may be used alone or in combination of two or more types.

As the radical polymerization initiator to be used for polymerization of the fluorinated diene compound (1), a polymerization initiator commonly used for radical polymerization of e.g. an azo compound, an organic peroxide or an inorganic peroxide, may be used. Specifically, diisopropyl peroxydicarbonate, an azo compound such as 2,2'-azobis(2-amidinopropane) dihydrochloride, 4,4'-azobis(4-cyanopentanoic acid), 2,2'-azobis(4-methoxy-2,3-dimethylvaleronitrile) or 1,1'-azobis(1-cyclohexanecarbonitrile), an organic peroxide such as benzoyl peroxide, perfluorobenzoyl peroxide, perfluorononanoyl peroxide or methyl ethyl ketone peroxide, or an inorganic peroxide such as $K_2S_2O_8$ or $(NH_4)_2S_2O_8$, may, for example, be mentioned.

The polymerization method is not particularly limited, and it may, for example, be a polymerization wherein the fluorinated diene compound (1) is directly polymerized (so-called bulk polymerization), a solution polymerization wherein the fluorinated diene compound (1) is dissolved in a fluorinated hydrocarbon, a chlorinated hydrocarbon, a chlorinated fluorohydrocarbon, an alcohol, a hydrocarbon or other organic solvents and polymerized, a suspension polymerization wherein polymerization is carried out in an aqueous medium, if necessary, in the presence of an organic solvent, or an emulsion polymerization wherein polymerization is carried out in an aqueous medium in the presence of an emulsifier. The temperature and the pressure for the polymerization are not particularly limited, and it is advisable to suitably set them taking into consideration the boiling point of the fluorinated diene compound, the heating source, removal of the polymerization heat, etc. The polymerization temperature is usually preferably from 0 to 200° C., particularly preferably from 30 to 100° C. The polymerization pressure may be a reduced pressure or an elevated pressure, and it is practically preferably from atmospheric pressure to about 10 MPa, more preferably from atmospheric pressure to about 5 MPa.

The fluoropolymer of the present invention has characteristics such that it is excellent in transparency, the glass transition temperature is high, and the heat resistance is high. By utilizing such characteristics, the fluoropolymer of the present invention is useful by itself as an optical resin material excellent in heat resistance, to be used for an optical fiber, an optical waveguide or an optical transmitter such as a lens. Further, the fluoropolymer of the present invention has characteristics that it is optically transparent, and it has a low refractive index as compared with a conventional transparent fluorocarbon resin (such as CYTOP, trade name, manufactured by Asahi Glass Company, Limited or Teflon AF, trade name, manufactured by DuPont). By utilizing such characteristics, the fluoropolymer of the present invention may be combined with a conventional transparent fluorocarbon resin having a low refractive index and use as a high performance optical device excellent in optical transparency, such as an optical fiber or an optical waveguide.

Particularly, a plastic optical fiber comprising a core made of a mixture comprising the fluoropolymer of the present invention and a refractive index-increasing agent, and a clad made of the fluoropolymer of the present invention, has excellent heat resistance. Such a plastic optical fiber may be used as of a step index type or a refractive index-distribution type, and it is particularly preferably a plastic optical fiber of refractive index-distribution type. As the above refractive index-increasing agent, a fluorinated low molecular weight compound is preferred, since the transparency of the obtainable mixture will be excellent. As such a fluorinated low molecular weight compound, perfluoro(triphenyltriazine), perfluoro(1,3,5-triphenylbenzene) or chlorotrifluoroethylene oligomer may, for example, be preferably mentioned. Such low molecular weight compounds may be used alone or in combination as a mixture of two or more of them.

The following methods may be mentioned as the method for producing a plastic optical fiber of refractive index-distribution type.

For example, a method wherein a columnar molded product of the fluoropolymer of the present invention is prepared so that at the center axis portion, a refractive index-increasing agent is present at a predetermined concentration, and the refractive index-increasing agent is diffused in a radial direction from the center axis portion by thermal diffusion to form a refractive index distribution, whereupon the obtained columnar molded product is used as a preform to form an optical fiber (JP-A-8-5848).

A method wherein a cylindrical molded product is prepared by the fluoropolymer of the present invention, a predetermined amount of a refractive index-increasing agent is introduced into the center portion, followed by thermal diffusion to form a cylindrical preform having a refractive index distribution, which is formed into an optical fiber (JP-A-8-334633).

Further, the fluoropolymer of the present invention is soluble in a fluorocarbon solvent such as perfluoro(2-butyltetrahydrofuran), perfluorooctane, perfluorohexane, perfluoro(tributylamine), perfluoro(tripropylamine), perfluorobenzene or dichloropentafluoropropane. A solution having the fluoropolymer of the present invention dissolved in such a solvent, is a fluoropolymer solution useful for various applications. As an application of such a solution, an application may, for example, be mentioned wherein it is coated on a substrate such as a glass or silicon wafer by a spin coating method or a spraying method, and then the solvent is vaporized for drying to form a thin film. The amount of the fluoropolymer contained in such a fluoropolymer solution is preferably from 0.01 to 20 mass %, particularly preferably from 0.1 to 10 mass %.

Further, the fluoropolymer of the present invention may be subjected to heat treatment or fluorine gas treatment, whereby the terminal groups can easily be substituted. And, by changing the structure of terminal groups by the treating method, the adhesion property to various substrates can be changed. For example, carboxyl groups can be introduced to the terminals by heating the fluoropolymer of the present invention at a temperature of at least 200° C. in the presence of air, followed by treatment with water. Otherwise, it is possible to remove reactive functional groups at the terminals by reacting them with fluorine gas, whereby it is possible to improve the thermal stability of the fluoropolymer.

EXAMPLES

Now, the present invention will be described in further detail with reference to Examples. However, it should be understood that the present invention is by no means restricted by such Examples. In the following, gas chromatography will be referred to as GC, a nuclear magnetic resonance spectrum analysis as NMR, a gas chromatography mass spectrum as GC-MS, tetramethylsilane as TMS, 1,1,2-trichlorotrifluoroethane as R-113, and dichloropentafluoropropane as R-225. Further, the GC purity is meant for the purity obtained from the peak area ratio by gas chromatography. Further, the refractive index was measured by means of Abbe's refractometer, and the glass transition temperature ($T_g$) was measured by means of a differential scanning calorimetry (DSC).

Example 1

Preparation of $CH_2=CHCH(OCH_3)CH_2OCOCF(CF_3)OCF_2CF_2CF_3$ $CH_2=CHCH(OCH_3)CH_2OH$ (270 g) was charged together with NaF (334 g) into a 2 L pressure resistant reactor equipped with a reflux condenser having a cooling medium of 20° C. circulated, and stirred at −10° C.

While bubbling nitrogen gas in the reactor to discharge HF formed as a by-product by the reaction, out of the system from the upper reflux condenser, $FCOCF(CF_3)OCF_2CF_2CF_3$ (1055 g) was dropwise added over a period of 1.5 hours. At that time, the temperature was adjusted so that the internal temperature of the reactor became at most 0° C. After completion of the dropwise addition, stirring was carried out at 30° C. for 18 hours to complete the reaction. After completion of the reaction, NaF contained in the crude solution was filtered off to obtain a crude product (981 g) (yield: 86.4%). As a result of the analysis by NMR, formation of the above identified compound was confirmed.

$^1$H-NMR (300.4 MHz, solvent: CDCl$_3$, standard: TMS) δ (ppm): 3.29 (s, 3H), 3.85 to 3.90 (m, 1H), 4.24 to 4.45 (m, 2H), 5.34 (s, 1H), 5.39 (d, J=8.4 Hz, 1H), 5.59 to 5.71 (m, 1H).

$^{19}$F-NMR (282.7 MHz, solvent: CDCl$_3$, standard: CFCl$_3$) δ (ppm): −81.8 (3F), −82.6 (3F), −79.9 to −87.5 (2F), −130.2 (2F), −132.3 (1F).

Example 2

Preparation of $CH_2ClCHClCH(OCH_3)CH_2OCOCF(CF_3)OCF_2CF_2CF_3$ $CH_2=CHCH(OCH_3)CH_2OCOCF(CF_3)OCF_2CF_2CF_3$ (981 g) obtained in Example 1, was charged into a 2 L three-necked flask cooled to 0° C. and equipped with a Dimroth condenser, and with stirring at from −10 to 0° C., chlorine gas was introduced at a rate of 0.8 g/min to carry out the reaction. When 170 g of chlorine gas was introduced, the reaction was terminated to obtain a crude liquid (1084 g).

The obtained crude liquid was purified by distillation under a reduced pressure of from 0.8 to 0.9 kPa (absolute pressure) to obtain a product (744 g). As a result of the analyses by NMR and GC, it was confirmed that the above identified compound was formed as a mixture of three types of diastereomers having a GC purity of 98%.

$^1$H-NMR (300.4 MHz, solvent: CDCl$_3$, standard: TMS) δ (ppm): 3.45 (d, J=1.5 Hz) and 3.47 (s) and 3.55 (d J=0.6 Hz) total 3H, 3.56 to 3.80 (m, 2H), 3.82 to 4.12 (m, 2H), 4.43 to 4.57 (m, 1H), 4.65 (dd, J=6.3 Hz, 11.4 Hz) and 4.89 (ddd, J=42.4 Hz, 12.0 Hz, 3.0 Hz) and 5.49 (q, J=5.1 Hz) total 1H.

$^{19}$F-NMR (376.0 MHz, solvent: CDCl$_3$, standard: CFCl$_3$) δ (ppm): −79.93 to −80.65 (1F), −81.72 to −81.80 (3F), −82.47 to −82.56 (3F), −86.46 to −87.22 (1F), −130.07 to −130.19 (2F), −132.26 to −132.47 (1F).

Example 3

Preparation of $CF_2ClCFClCF(OCF_3)CF_2OCOCF(CF_3)OCF_2CF_2CF_3$ by a Fluorination Reaction Into a 3 L autoclave made of nickel, $CF_3CF_2CF_2OCF(CF_3)CF_2OCF(CF_3)COF$ (3523 g, hereinafter referred to as the solvent A) was charged, stirred and maintained at 5° C. At the gas outlet of the autoclave, a condenser maintained at −10° C. was installed. Nitrogen gas was blown thereinto for 3.5 hours, and then fluorine gas diluted with nitrogen gas to 20% (hereinafter referred to as the diluted fluorine gas) was blown thereinto at a flow rate of 26.52 L/hr for one hour. Then, while supplying fluorine gas at the same flow rate, a part (415 g) of $CH_2ClCHClCH(OCH_3)CH_2OCOCF(CF_3)OCF_2CF_2CF_3$ obtained in Example 2 was injected over a period of 22.5 hours. The reaction crude liquid (261 g) was withdrawn.

Then, while supplying the diluted fluorine gas at the same flow rate, $CH_2ClCHClCH(OCH_3)CH_2OCOCF(CF_3)OCF_2CF_2CF_3$ (642 g) was injected over a period of 22.0 hours. A reaction crude liquid (533 g) was withdrawn.

Further, while supplying the diluted fluorine gas at the same flow rate, $CH_2ClCHClCH(OCH_3)CH_2OCOCF(CF_3)OCF_2CF_2CF_3$ (471 g) was injected over a period of 22.8 hours. The reaction crude liquid (270 g) was withdrawn.

Then, while supplying the diluted fluorine gas at the same flow rate, the reaction temperature was adjusted at 25° C. for 22 hours. Then, nitrogen gas was blown thereinto for 3.0 hours. The reaction crude liquid (3530 g) was recovered. As a result of the analysis of the reaction crude liquid by GC-MS, it was found that the solvent A and the above identified compound were obtained as the main components. The reaction yield of the above identified compound was 71%.

Example 4

Preparation of $CF_2ClCFClCF(OCF_3)COF$ (2-3) by a Decomposition Reaction of an Ester Bond Into a 300 mL four-necked flask equipped with a stirrer and a reflux condenser, $CF_2ClCFClCF(OCF_3)CF_2OCOCF(CF_3)OCF_2CF_2CF_3$ (200 g, 0.31 mol) obtained in Example 3 was charged together with KF powder (9.0 g, 0.155 mol), and while stirring sufficiently, the mixture was heated in an oil bath at a temperature of from 90 to 95° C. for from 0.5 to 1 hour. After confirming refluxing formed as the reaction proceeded, the reaction system was brought to reduced pressure, and the formed product was recovered by distilling it and withdrawing it from the reaction system over a period of 5 hours. Further, the crude product was distilled to obtain the above identified compound (74 g) having a GC purity of 99.9% (yield: 79%). From the NMR spectrum, it was confirmed that the above identified compound is the main component.

$^{19}$F-NMR (282.7 MHz, solvent: $CDCl_3$, standard: $CFCl_3$) δ (ppm): 28.4, 28.0 (1F), −55.1, −55.4 (3F), −61.6 to −63.9 (2F), −121.9, −123.9 (1F), −128.7, −129.0 (1F).

Boiling point: 62° C./33.3 kPa (absolute pressure)

Example 5

Preparation of $CF_2ClCFClCF(OCF_3)CF_2OCF(CF_3)COF$ (2-2)

Into an autoclave made of a hastelloy alloy and having an internal capacity of 100 mL, KF (0.4 g, 7.14 mmol) was put, and after reducing the pressure, $CF_2ClCFClCF(OCF_3)COF$ obtained in Example 4 (37 g, 0.12 mol) and tetraglime (10 g) were charged and cooled with sufficient stirring, followed by stirring for from 30 minutes to one hour while adjusting the internal temperature to from −5° C. to +5° C. Then, the autoclave was connected to a steel bottle of hexafluoropropylene oxide, and hexafluoropropylene oxide (33 g) was added while maintaining the internal temperature at at most 25° C. and the internal pressure at about 0.2 MPa, followed by stirring until no decrease of the internal pressure was observed. Thereafter, hexafluoropropylene oxide was purged, followed by stirring at 25° C. for from 1 to 2 hours. Then, the autoclave was opened, and the remaining solid was removed by filtration, followed by phase separation to obtain a crude product. The crude product was further distilled to obtain 5.9 g (yield: 10%) of pure $CF_2ClCFClCF(OCF_3)CF_2OCF(CF_3)COF$.

$^{19}$F-NMR (282.7 MHz, solvent: $CDCl_3$, standard: $CFCl_3$) δ (ppm); 28.0, 27.8, 27.4 (1F), −52.2 to −53.0 (3F), −63.0 to −66.5 (2F), −79.5 to −81.5 (2F), −81.2, −81.4 (3F), −128.1, −128.7 (1F), −129.2, −130.1 (1F), −131.4, −132.1 (1F).

Example 6-1

Preparation of $CF_2ClCFClCF(OCF_3)CO_2CH_3$ (3-2)

Into a 1 L four-necked flask made of glass and equipped with a stirrer, a reflux condenser and a dropping funnel, methanol (120 g, 3.75 mol) was put and cooled until the internal temperature became from 5 to 10° C., and while sufficiently stirring, $CF_2ClCFClCF(OCF_3)CF_2OCOCF(CF_3)OCF_2CF_2CF_3$ (380 g, 0.59 mol) obtained in Example 3 was dropwise added while maintaining the internal temperature at from 5 to 20° C. Thereafter, while bubbling nitrogen gas in the reactor to discharge HF formed as a by-product by the reaction out of the system by an upper reflux condenser, stirring was continued for a while at room temperature. Then, deionized water (340 g) was added, followed by stirring sufficiently and then by phase separation into two phases, whereupon the product of the lower layer was withdrawn. Further, the crude product was distilled to obtain 128 g of pure $CF_2ClCFClCF(OCF_3)CO_2CH_3$ (yield: 67%).

Example 6-2

Preparation of $CF_2ClCFClCF(OCF_3)CO_2CH_3$ (3-2)

Using $CF_2ClCFClCF(OCF_3)COF$ obtained in Example 4 (40 g, 0.12 mol) and methanol (10 g, 0.31 mol), in the same manner as in Example 6-1, $CF_2ClCFClCF(OCF_3)CO_2CH_3$ was obtained (36 g, yield: 94%).

$^{19}$F-NMR (282.7 MHz, solvent: $CDCl_3$, standard: $CFCl_3$) δ (ppm); −55.1, −55.5 (3F), −61.8 to −64.4 (2F), −123, −126 (1F), −129.3, −129.7 (1F).

$^{1}$H-NMR (300.4 MHz, solvent: $CDCl_3$, standard: TMS) δ (ppm); 3.96 ($CH_3$).

Boiling point: 55° C./2.7 kPa.

Example 7

Preparation of $CF_2ClCFClCF(OCF_3)CH_2OH$ (3-3) by a Reduction Reaction

Into a 2 L four-necked flask made of glass and quipped with a stirrer and a dropping funnel, sodium boron hydride (17 g, 0.46 mol), diethyl ether (230 g) and ethanol (200 g) were put, followed by cooling until the internal temperature became from 5 to 10° C. While maintaining the internal temperature at from 5 to 20° C. with sufficient stirring, $CF_2ClCFClCF(OCF_3)CO_2CH_3$ (150 g, 0.46 mol) obtained in Example 6 was dropwise added. Thereafter, while maintaining the internal temperature at from 5 to 20° C., the reaction solution was stirred for from 2 to 3 hours. Then, 1 mol/L of hydrochloric acid (310 g) was added, followed by stirring sufficiently, and extraction was carried out with diethyl ether. The organic layer was separated and dried over magnesium sulfate, whereupon diethyl ether was distilled off under reduced pressure. The obtained crude product was purified by distillation to obtain 128 g (yield: 70%) of highly pure $CF_2ClCFClCF(OCF_3)CH_2OH$.

$^{19}$F-NMR (282.7 MHz, solvent: $CDCl_3$, standard: $CFCl_3$) δ (ppm); −53.3, −53.8 (3F), −60.8 to −63.6 (2F), −125.4, −126.7 (1F), −128.9, −129.3 (1F).

$^1$H-NMR (300.4 MHz, solvent: $CDCl_3$, standard: TMS) δ (ppm); 2.1 (OH), 4.0 to 4.3 ($CH_2$).

Boiling point: 41° C./0.7 kPa (absolute pressure).

Example 8

Preparation of $CF_2ClCFClCF(OCF_3)CH_2OCF=CF_2$ (3-4)

Into a 2 L four-necked flask equipped with a stirrer and a dropping funnel, sodium hydride (5.4 g, 0.13 mol) was charged, and in an inert gas atmosphere, diethyl ether (140 mL) was charged. Then, while adjusting the internal temperature from 0 to 5° C., $CF_2ClCFClCF(OCF_3)CH_2OH$ (35 g, 0.12 mol) obtained in Example 7 was slowly dropwise added. Thereafter, the internal temperature was slowly raised to room temperature, and the reaction was carried out for 5 hours. Thereafter, the reaction solution was transferred to a 2L autoclave which was preliminarily vacuumed, and introducing nitrogen to 0.5 MPa, followed by purging, was repeated three times. Then, while maintaining the remaining nitrogen pressure at 0.05 MPa, tetrafluoroethylene (47 g, 0.47 mol) was slowly introduced little by little. After the charging, the reaction temperature was raised to 70° C. to raise the internal pressure to 2.2 MPa, and the reaction was carried out for from 5 to 10 hours until no more pressure decrease was observed. Then, the reaction system was cooled, and remaining tetrafluoroethylene was purged, whereupon the autoclave was opened.

As post-treatment of the reaction solution, methanol (9.0 g) and 1 mol/L of hydrochloric acid (140 g) were added, followed by sufficient stirring, whereupon extraction with diethyl ether was carried out, and the organic layer was separated and then, dried over magnesium sulfate, and diethyl ether was distilled off under reduced pressure.

The crude product thus obtained was purified by distillation to obtain pure $CF_2ClCFClCF(OCF_3)CH_2OCF=CF_2$ (18 g, yield: 40%).

$^{19}$F-NMR (282.7 MHz, solvent: $CDCl_3$, standard: $CFCl_3$) δ (ppm); −53.3, −53.5 ($F^e$, 3F), −60.8 to −63.6 ($F^i$, 2F), −120.2 ($F^a$, 1F, $J_{ab}$=99 Hz), −124.7, −126.0 ($F^g$, 1F), −126.0 ($F^b$, 1F, $J_{bc}$=108 Hz), −128.9, −129.1 ($F^d$, 1F), −137.4 ($F^c$, 1F, $J_{ac}$=58 Hz).

Here, a to i in $F^a$ to $F^i$, correspond to the positions of fluorine atoms, as shown in the following formula:

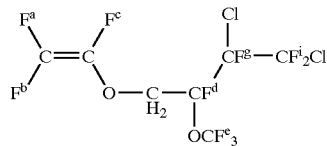

$^1$H-NMR (300.4 MHz, solvent: $CDCl_3$, standard: TMS) δ (ppm); 4.4 to 4.7 ($CH_2$).

Boiling point: 41° C./1.3 kPa (absolute pressure).

Example 9

Preparation of $CF_2ClCFClCF(OCF_3)CH_2OCFClCF_2Cl$ (3-5)

Into a 100 mL three-necked flask equipped with a stirrer and a dry ice condenser, $CF_2ClCFClCF(OCF_3)$ $CH_2OCF=CF_2$ (35 g, 92 mmol) obtained in Example 8 was charged and cooled until the internal temperature became within a range of from −25 to −20° C., and while maintaining the internal temperature at −10° C. to +10° C. with sufficient stirring, chlorine gas was blown thereinto. When chlorine (7.4 g, 104 mmol) gas was introduced, the introduction was stopped, and the crude product was recovered. The crude product was further distilled to obtain pure $CF_2ClCFClCF(OCF_3)CH_2OCFClCF_2Cl$ (38 g, yield: 95%).

$^{19}$F-NMR (282.7 MHz, solvent: $CDCl_3$, standard: $CFCl_3$) δ (ppm); −53.3, −53.5 (3F), −60.8 to −63.6 (2F), −69.2 (2F), −74.2, −74.5 (1F), −123.3 to −124.9 (1F), −128.9, −129.0 (1F).

$^1$H-NMR (300.4 MHz, solvent: $CDCl_3$, standard: TMS) δ (ppm); 4.4 to 4.7 ($CH_2$).

Boiling point: 50° C./0.7 kPa (absolute pressure)

Example 10

Preparation of $CF_2ClCFClCF(OCF_3)CF_2OCFClCF_2Cl$ (3-1)

Into a 500 mL autoclave made of nickel, R-113 (312 g) was charged, stirred and maintained at 25° C. At the gas outlet of the autoclave, a condenser maintained at 20° C., a NaF pellet-packed layer and a condenser maintained at −10° C. were installed in series. Further, a liquid-returning line was installed to return the liquid condensed from the condenser maintained at −10° C., to the autoclave. Nitrogen gas was supplied for 1.0 hour, and then, diluted fluorine gas was supplied at a flow rate of 11.88 L/hr for one hour. Then, while supplying fluorine gas at the same flow rate, a solution having $CF_2ClCFClCF(OCF_3)CH_2OCFClCF_2Cl$ (34 g, 75 mmol) obtained in Example 9, dissolved in R-113 (195.3 g), was injected over a period of 5.8 hours.

Then, while supplying fluorine gas at the same flow rate and maintaining the reactor pressure at 0.15 MPa, a R-113 solution having a benzene concentration of 0.01 g/ml was injected in an amount of 9 ml while raising the temperature from 25° C. to 40° C., whereupon the benzene inlet of the autoclave was closed, and stirring was continued for 0.3 hour. Then, while maintaining the reactor pressure at 0.15 MPa and the internal temperature of the reactor at 40° C., the above-mentioned benzene solution was injected in an amount of 6 ml, and stirring was continued for 0.3 hour. Further, while maintaining the internal temperature of the reactor at 40° C., the above-mentioned benzene solution was injected in an amount of 6 ml, and stirring was continued for 0.3 hour. The same operation was repeated seven times, and stirring was continued for further 0.7 hour. The total amount of benzene injected was 0.595 g, and the total amount of R-113 injected was 57 ml. Further, nitrogen gas was supplied for 1.0 hour. The desired product was quantified by $^{19}$F-NMR (internal standard: $C_6F_6$), whereby the yield of the above identified compound was 85%. The crude product was further distilled to obtain 30 g of pure $CF_2ClCFClCF(OCF_3)CF_2OCFClCF_2Cl$.

$^{19}$F-NMR (282.7 MHz, solvent: $CDCl_3$, standard: $CFCl_3$) δ (ppm); −52.4, −52.8 (3F), −60.7 to −64.2 (2F), −70.5 (2F), −76.5 (1F), −76.7 to −81.2 (2F) −127.7, −128.5 (1F), −132.9, −133.7 (1F).

Boiling point: 35° C./0.5 kPa (absolute pressure).

Example 11

Preparation of $CF_2=CFCF(OCF_3)CF_2OCF=CF_2$

Into a three-necked flask made of glass, having an internal capacity of 100 mL and equipped with a stirrer, a reflux condenser and a dropping funnel, zinc (13 g, 200 mmol) was put, and 32 g of dimethyl formamide was put. Then, the system was vacuumed to 27 kPa (absolute pressure), and further, the internal temperature was adjusted to from 65 to 70° C. $CF_2ClCFCClCF(OCF_3)CF_2OCFClCF_2Cl$ (12 g, 25 mmol) obtained in Example 10 was slowly dropwise added thereto from the dropping funnel, and during the reaction, the product was distilled and quickly withdrawn. Thereafter, the crude product was fractionated to obtain pure $CF_2=CFCF(OCF_3)CF_2OCF=CF_2$ (4.0 g, yield: 47%).

$^{19}$F-NMR (282.7 MHz, solvent: $CDCl_3$, standard: $CFCl_3$) δ (ppm); −55.4 ($F^f$, 3F) −86.5 ($F^h$, 1F, $J_{hi}$=48 Hz), −87.0 to −88.6 ($F^d$, 2F), −103.2 ($F^i$, 1F, $J_{gi}$=116 Hz), −113.0 ($F^a$, 1F, $J_{ab}$=83 Hz), −121.3 ($F^b$, 1F, $J_{bc}$=111 Hz), −134.2 ($F^c$, 1F, $J_{ac}$=65 Hz), −134.4 ($F^e$, 1F), −184.0 ($F^g$, 1F, $J_{gh}$=39 Hz). Here, a to i of $F^a$ to $F^i$ correspond to the positions of the fluorine atoms shown in the following formula:

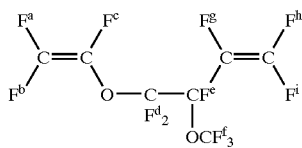

IR: 1785 cm$^{-1}$ ($CF_2=CF-$), 1838 cm$^{-1}$ ($CF_2=CFO-$).
Boiling point: 30° C./25.3 kPa (absolute pressure).

Example 12

Preparation of a Polymer by Polymerization of $CF_2=CFCF(OCF_3)CF_2OCF=CF_2$ $CF_2=CFCF(OCF_3)CF_2OCF=CF_2$ (0.5 g) obtained in Example 11 and perfluorobenzoyl peroxide (1.5 mg) were put in a glass ampule, frozen in liquid nitrogen, vacuum deaerated and then sealed. The ampule was heated in a warm water bath at 50° C. for 220 hours, whereupon the solidified content was taken out, and the remaining monomer was recovered under vacuum and then dried at 200° C. for 1 hour. The yield of the obtained polymer (hereinafter referred to as the polymer A1) was 43%. A part of the polymer A1 was dissolved in perfluoro(2-butyltetrahydrofuran) (hereinafter referred to as PBTHF), and the intrinsic viscosity was measured and found to be 0.268 dl/g. The molecular weight of the polymer was such that the number average molecular weight ($M_n$) was 102000, and the weight average molecular weight ($M_w$) was 201500.

The refractive index of the film of the polymer $A_1$ prepared by press molding was 1.334, and $T_g$ was 113° C. The tensile characteristics of the polymer A1 were measured, whereby the tensile modulus was 1325 MPa, the yield stress was 35 MPa, and the breaking elongation was 3.9%. Further, the zero share viscosity at 230° C. was measured by a rotary melt viscosity-measuring apparatus and found to be 5500 Pa·s. The glass transition temperature, as measured by a differential scanning calorimetry (DSC), of a polymer obtained by polymerizing monomer $CF_2=CFCF_2CF_2OCF=CF_2$ (hereinafter referred to as PBVE) under the same conditions, was 108° C., whereby improvement of the glass transition temperature of the polymer A1 was confirmed.

Further, the infrared absorption spectrum of the polymer was measured, whereby absorption at 1785 cm$^{-1}$ attributable to $CF_2=CF-$ and at 1838 cm$^{-1}$ attributable to $CF_2=CFO-$, as observed with the monomer, was found to have disappeared. This polymer A1 was found to have no pendant double bond, be free from a crosslinking reaction, have a high conversion and be completely soluble in R225 and thus found to be a cyclic polymer. Further, from the $^{19}$F-NMR analysis, it was confirmed to be a polymer having repeating units of the following structure. The polymer was found to be excellent in transparency and useful as an optical resin material for e.g. an optical fiber or an optical waveguide.

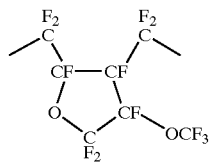

Example 13

Preparation of Polymer A2

$CF_2=CFCF(OCF_3)CF_2OCF=CF_2$ (0.2 g) and diisopropyl peroxy dicarbonate (5 mg) were put into a glass ampule, frozen in liquid nitrogen, vacuum deaerated and then sealed. The ampule was heated in a warm water bath at 40° C. for 20 hours, whereupon a solidified content was taken out and dried at 200° C. for 1 hour. The yield of the obtained polymer (hereinafter referred to as the polymer A2) was 95%. A part of the polymer A2 was dissolved in PBTHF, and the intrinsic viscosity was measured and found to be 0.09 dl/g.

Example 14

Preparation of Polymer A3

Into an autoclave made of stainless steel and having an internal capacity of 200 mL, water (80 g), $CF_2=CFCF(OCF_3)CF_2OCF=CF_2$ (15 g, 43.6 mmol) and perfluorobenzoyl peroxide (38 mg) were charged. The autoclave was flushed with nitrogen and then heated until the internal temperature of the autoclave became 70° C., followed by polymerization for 20 hours. The obtained polymer was washed with deionized water and methanol, and then dried at 200° C. for 1 hour. The yield of the obtained polymer (hereinafter referred to as the polymer A3) was 70%.

A part of the polymer A3 was dissolved in PBTHF, and the intrinsic viscosity was measured and found to be 0.25 dl/g. The refractive index of a film of the polymer A3 prepared by press molding was 1.334, and $T_g$ was 113° C. The tensile characteristics of the polymer A3 were measured, whereby the tensile modulus was 1330 MPa, the yield stress was 35 MPa, and the breaking elongation was 3.5%. Further, the zero share viscosity at 230° C. was measured by a rotary melt viscoelasticity-measuring apparatus and found to be 5300 Pa·s.

Example 15

Preparation of Polymer B1 by Copolymerization of $CF_2=CFCF(OCF_3)CF_2OCF=CF_2$ with Tetrafluoroethylene Into a 200 mL autoclave made of stainless steel, R225 (80 mL), $CF_2=CFCF(OCF_3)CF_2OCF=CF_2$ (5.6 g, 16.3 mmol) and perfluorobenzoic peroxide (25 mg) were charged. While cooling the autoclave with liquid nitrogen, it was vacuumed by a vacuum pump, and the vacuum pump was detached, and the temperature was returned to room temperature, and then, again, while cooling with liquid nitrogen, it was vacuumed by a vacuum pump. This operation was repeated three times. Then, the internal temperature of the autoclave was returned to room temperature, whereupon tetrafluoroethylene (32 g, 320 mmol) was introduced. And, heating was carried out until the internal temperature became 70° C., followed by polymerization for 3 hours. Thereafter, the remaining tetrafluoroethylene was purged, and the remaining monomer was distilled off under reduced pressure, to obtain 29 g of a white polymer (hereinafter referred to as the polymer B1). The structure of the polymer B1 was analyzed, whereby it was found to be a polymer having a structure derived from $CF_2=CFCF(OCF_3)CF_2OCF=CF_2$ introduced in an amount of 1.4 mol % to a part of polytetrafluoroethylene.

$T_g$ of the polymer B1 was 130° C.

Example 16

Preparation of Polymer B2 by Copolymerization of $CF_2=CFCF(OCF_3)CF_2OCF=CF_2$ with PBVE Into an autoclave made of stainless steel and having an internal capacity of 200 mL, water (80 g), $CF_2=CFCF(OCF_3)CF_2OCF=CF_2$ (15 g), PBVE (15 g), perfluorobenzoyl peroxide (75 mg) and methanol (1.5 g) were charged. The autoclave was flushed with nitrogen and then heated until the internal temperature of the autoclave became 70° C., followed by polymerization for 20 hours. The obtained polymer (hereinafter referred to as the polymer B2) was washed with deionized water and methanol and then dried at 200° C. for 1 hour. The yield of the obtained polymer B2 was 80%.

A part of the polymer B2 was dissolved in PBTHF, and the intrinsic viscosity was measured and found to be 0.33 dl/g. The refractive index of a film of the polymer B2 prepared by press molding was 1.338, and $T_g$ was 110° C.

Example 17

Preparation of Polymer B3 by Copolymerization of $CF_2=CFCF(OCF_3)CF_2OCF=CF_2$ with PERFLUORO(2,2-DIMETHYL-1,3-DIOXOL) (Hereinafter Referred to as PDD)

Into an autoclave made of stainless steel and having an internal capacity of 200 mL, water (80 g), $CF_2=CFCF(OCF_3)CF_2OCF=CF_2$ (21 g), PDD (9 g), diisopropyl peroxy dicarbonate (75 mg) and methanol (1.5 g) were charged. The autoclave was flushed with nitrogen and then heated until the internal temperature of the autoclave became 40° C., followed by polymerization for 20 hours. The obtained polymer (hereinafter referred to as the polymer B3) was washed with deionized water and methanol and then dried at 200° C. for 1 hour. The yield of the obtained polymer B3 was 90%.

A part of the polymer B3 was dissolved in PBTHF, and the intrinsic viscosity was measured and found to be 0.36 dl/g. The refractive index of a film of the polymer B3 prepared by press molding, was 1.320, and $T_g$ was 158° C.

Example 18

Preparation of Optical Fiber

The polymer A3 (93 parts) obtained in Example 14 and perfluoro(triphenyltriazine) (7 parts) were put into a glass ampule, and after sealing, uniformly melt-mixed at 240° C. to obtain a polymer mixture (hereinafter referred to as the mixture C1). The refractive index of a film of the mixture C1 prepared by press molding, was 1.354, and Tg was 93° C.

Then, in accordance with the method disclosed in JP-A-8-5848, an optical fiber was prepared by using the mixture C1 and the polymer A3. Namely, firstly, the mixture C1 was melted in a sealed glass tube to obtain a columnar molded product (C1a). Then, the polymer A3 alone was melt-molded into a cylinder, and while inserting the molded product (C1a) into the hollow portion of this cylinder, the temperature was raised to 240° C. to join them to obtain a preform. This preform was melt-spun at 240° C. to obtain an optical fiber wherein the refractive index gradually decreases from the center portion towards the peripheral portion.

The optical transmission loss of the obtained optical fiber was measured by a cutback method, whereby it was 195 dB/km at 650 nm, 110 dB/km at 850 nm and 83 dB/km at 1300 nm, and it was an optical fiber capable of transmitting light from a visible light to a near infrared light excellently.

This optical fiber was heated and stored in an oven of 70° C. for 1000 hours and then withdrawn, whereupon the refractive index distribution was measured by an interfaco interference microscope and compared with the refractive index distribution before the heating and storing, whereby no change was observed. Further, the transmission band was measured by a pulse method to evaluate the transmission characteristics. The optical fiber was heated and stored at 70° C. for 1000 hours, whereupon the transmission band was measured, whereby it was 350 MHz-km both before and after the heating and storing, and no decrease of the band was observed, and thus it was confirmed that the heat resistance was excellent.

Example 19

Preparation of an Optical Fiber

By means of an extruder, dichroic extrusion was carried out so that a polymer of PBVE (intrinsic viscosity: 0.27 dl/g, refractive index: 1.342) was disposed at the center and the polymer A3 was disposed at the circumferential portion concentrically, thereby to spin a core/clad optical fiber. The obtained optical fiber had an outer diameter of 520 μm and a core diameter of 485 μm. Further, the optical transmission loss was measured by a cutback method, whereby it was 148 dB/km at 650 nm, 88 dB/km at 850 nm and 73 dB/km at 1300 nm, and thus, it was an optical fiber capable of transmitting light from a visible light to a near infrared light excellently.

Example 20

Preparation of an Optical Fiber

A hollow tube made of the polymer B3 was put on the preform obtained in Example 18, followed by melt spinning at 240° C. to obtain an optical fiber wherein the refractive index gradually decreases from the center portion towards the peripheral portion. The optical transmission loss of the obtained optical fiber was measured by a cutback method, whereby it was 143 dB/km at 650 nm, 61 dB/km at 850 nm and 35 dB/km at 1300 nm, and it was confirmed to be an optical fiber capable of transmitting light from a visible light to a near infrared light excellently. Further, the increase of the loss at a bending radius of 10 mm of this optical fiber was measured at 850 nm and found to be 0.14 dB, and thus, it was found to be an optical fiber having a small bending loss.

This optical fiber was heated and stored in an oven of 70° C. for 1000 hours, whereupon the transmission loss was measured, whereby no change was observed. Further, the transmission band was measured by a pulse method to evaluate the transmission characteristics. The transmission band was measured after heating and storing the optical fiber at 70° C. for 1000 hours, whereby it was 275 MHz·km both before and after the heating and storing, and no decrease of the band was observed, and thus it was confirmed that the heat resistance was excellent.

Example 21

Preparation of Polymer D1

PDD and tetrafluoroethylene were subjected to radical polymerization in a mass ratio of 80:20 by using PBTHF as a solvent, to obtain a polymer which has $T_g$ of 160° C. and $M_n$ of $1.7 \times 10^5$. This polymer was subjected to heat treatment at 250° C. for 5 hours in an atmosphere of a fluorine/nitrogen mixed gas (fluorine gas concentration: 20 vol %), to obtain a polymer (hereinafter referred to as the polymer $D_1$) having good light transmittance and thermal stability. The polymer D1 was colorless transparent, and the refractive index was 1.305.

Example 22

Preparation of an Optical Fiber

By means of an extruder, dichroic extrusion was carried out so that the polymer A3 was disposed at the center portion and the polymer D1 was disposed at the circumferential portion concentrically, to spin an optical fiber of core/clad type. The obtained optical fiber had an outer diameter of 990 μm and a core diameter of 905 μm. Further, the optical transmission loss was measured by a cutback method, whereby it was 189 dB/km at 650 nm, 98 dB/km at 850 nm, and 75 dB/km at 1300 nm, and thus it was an optical fiber capable of transmitting light from a visible light to a near infrared light excellently.

Example 23

Preparation of an Optical Fiber 92.5 parts of the polymer A3 and 7.5 parts of perfluoro (1,3,5-triphenylbenzene) were put into a glass ampule, sealed and uniformly melt-mixed at 250° C. to obtain a polymer mixture (hereinafter referred to as the mixture C2). The refractive index of a film made of the mixture C2 prepared by press molding, was 1.350, and $T_g$ was 95° C.

Then, an optical fiber was prepared by using the mixture C2 and the polymer A3. Namely, firstly, the mixture C2 was melted in a glass sealed tube to obtain a columnar molded product C2a. Then, a cylinder was melt-molded solely by the polymer A3, and while inserting the molded product C2a in the hollow portion of this cylinder, heating was carried out at 220° C. to join them to obtain a preform. This preform was melt-spun at 240° C. to obtain an optical fiber wherein the refractive index gradually decreases from the center portion towards the peripheral portion.

The optical transmission loss of the obtained optical fiber was measured by a cutback method. Whereby it was 185 dB/km at 650 nm, 96 dB/km at 850 nm, and 82 dB/km at 1300 nm, and thus, it was an optical fiber capable of transmitting light from a visible light to a near infrared light excellently.

This optical fiber was heated and stored in an oven of 70° C. for 2000 hours, and then taken out, whereupon the refractive index distribution was measured by an interface interference microscope, and compared with the refractive index distribution before the heating and storing, whereby no change was observed. Further, the transmission characteristics were evaluated by measuring the transmission band by a pulse method. The optical fiber was heated and stored at 70° C. for 2000 hours, whereupon the transmission band was measured, whereby it was 335 MHz·km both before and after the heating and storing, and no decrease of the band takes place, and it was confirmed that the heat resistance was good.

Example 24

Preparation of an Optical Fiber 90 parts of the polymer A3 and 10 parts of chlorotrifluoroethylene oligomer were put into a glass ampule and, after sealing, uniformly melt-mixed at 250° C. to obtain a polymer mixture (hereinafter referred to as the mixture C3). The refractive index of a film of the mixture C3 prepared by press molding was 1.345, and $T_g$ was 84° C.

Then, an optical fiber was prepared by using the mixture C3 and the polymer A3. Namely, firstly, the mixture C3 was melted in a sealed glass tube to obtain a columnar molded product C3a. Then, the polymer A3 alone was melt-molded into a cylinder, and while inserting the molded product C3a into the hollow portion of this cylinder, heating at 220° C. was carried out to join them to obtain a preform. This preform was melt-spun at 240° C. to obtain an optical fiber wherein the refractive index gradually decreases from the center portion towards the peripheral portion.

The optical transmission loss of the obtained optical fiber was measured by a cutback method, whereby it was 125 dB/km at 650 nm, 71 dB/km at 850 nm, and 53 dB/km at 1300 nm, and thus, it was an optical fiber capable of transmitting light from a visible light to a near infrared light excellently.

This optical fiber was heated and stored in an oven of 70° C. for 1000 hours and then, withdrawn, whereupon the refractive index distribution was measured by an interface interference microscope and compared with the refractive index distribution prior to the heating and storing, whereby no change was observed. Further, the transmission characteristics were evaluated by measuring the transmission band by a pulse method. The transmission band was measured after heating and storing the optical fiber at 70° C. for 1000 hours, whereby it was 328 MHz-km both before and after the heating and storing, and no decrease of the transmission band was observed, whereby it was confirmed that the heat resistance was excellent.

INDUSTRIAL APPLICABILITY

According to the present invention, a novel fluoropolymer which can be an optical resin material having a low refractive index, excellent heat resistance and a high glass transition temperature as compared with a conventional polymer of a fluorinated diene having no side chain, and a novel fluorinated diene compound having two unsaturated bonds, capable of presenting such a fluoropolymer, can be provided. Further, by dissolving the fluoropolymer in a certain specific fluorocarbon solvent, it is possible to provide a useful fluoropolymer solution. Further, the fluoropolymer has a low refractive index and excellent heat resistance, whereby a high performance optical transmitter and a plastic optical fiber can be provided.

The entire disclosure of Japanese Patent Application No. 2001-334352 filed on Oct. 31, 2001 including specification, claims and summary is incorporated herein by reference in its entirety.

What is claimed is:

1. A fluorinated diene compound represented by the following formula (1):

$$CF_2=CFCF(OR^f)CF_2OCF=CF_2 \qquad (1)$$

wherein $R^f$ is a perfluoroalkyl group.

2. The fluorinated diene compound according to claim 1, wherein $R^f$ is a trifluoromethyl group.

3. A method for producing a fluorinated diene compound represented by the following formula (1), characterized in that a dehalogenation reaction is carried out at halogen atoms other than fluorine atoms in at least one compound selected from a compound represented by the following formula (2) and a compound represented by the following formula (3):

$$CF_2=CFCF(OR^f)CF_2OCF=CF_2 \qquad (1)$$

$$CF_2Z^1CFZ^2CF(OR^f)CF_2OCF=CF_2 \qquad (2)$$

$$CF_2Z^1CFZ^2CF(OR^f)CF_2OCFZ^3CF_2Z^4 \qquad (3)$$

wherein $R^f$ is a perfluoroalkyl group, and each of $Z^1$, $Z^2$, $Z^3$ and $Z^4$ which are independent of one another, is a halogen atom other than a fluorine atom.

4. A fluoropolymer comprising monomer units formed by cyclopolymerization of a fluorinated diene compound represented by the formula (1), or monomer units formed by cyclopolymerization of a fluorinated diene compound represented by the formula (1) and monomer units formed by polymerization of other monomer polymerizable with the fluorinated diene compound represented by the formula (1):

$$CF_2=CFCF(OR^f)CF_2OCF=CF_2 \qquad (1)$$

wherein $R^f$ is a perfluoroalkyl group.

5. The fluoropolymer according to claim 4, wherein $R^f$ is a trifluoromethyl group.

6. The fluoropolymer according to claim 4, wherein the monomer units formed by the cyclopolymerization of the fluorinated diene monomer represented by the formula (1), are monomer units represented by any one of the following formulae, wherein $R^f$ is as defined above:

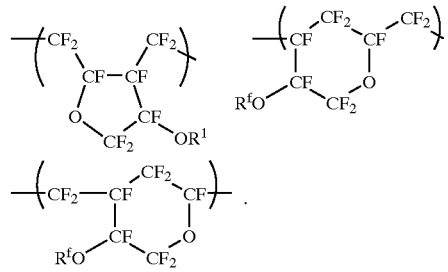

7. The fluoropolymer according to claim 4, wherein the monomer units of other polymerizable monomer are monomer units formed by polymerization of at least one member selected from a fluorinated diene which is cyclopolymerizable, other than the fluorinated diene compound represented by the formula (1), a monomer having a fluorinated aliphatic cyclic structure, a fluorinated non-cyclic vinyl ether monomer and a fluoroolefin.

8. The fluoropolymer according to claim 4, wherein the other monomer units are monomer units formed by polymerization of at least one member selected from tetrafluoroethylene, perfluoro(butenyl vinyl ether) and perfluoro(2,2-dimethyl-1,3-dioxole).

9. A fluoropolymer solution having the fluoropolymer as defined in claim 4 dissolved in at least one fluorocarbon solvent selected from perfluoro(2-butyltetrahydrofuran), perfluorooctane, perfluorohexane, perfluoro(tributylamine), perfluoro(tripropylamine), perfluorobenzene and dichloropentafluoropropane.

10. An optical transmitter made by using the fluoropolymer as defined in claim 4.

* * * * *